United States Patent [19]

Nishimura et al.

[11] Patent Number: 5,281,641

[45] Date of Patent: Jan. 25, 1994

[54] DENTAL OR SURGICAL ADHESIVE FILLER

[75] Inventors: Hiroshi Nishimura; Shousuke Ito, both of Kyoto; Masao Nakano, Nagaokakyo; Sunao Kaneda, Kyoto; Kayoko Adachi, Mishima, all of Japan

[73] Assignee: Mitsui Petrochemical Industries, Ltd., Tokyo, Japan

[21] Appl. No.: 29,635

[22] Filed: Mar. 11, 1993

[30] Foreign Application Priority Data

Mar. 13, 1992 [JP] Japan .................................. 4-088305

[51] Int. Cl.⁵ .............................................. C08K 5/55
[52] U.S. Cl. .................................. 524/183; 523/116; 523/118; 525/251
[58] Field of Search ................ 523/116, 118; 524/183; 525/251

[56] References Cited

U.S. PATENT DOCUMENTS 4,639,498 1/1987 Ritter ................................. 525/251

FOREIGN PATENT DOCUMENTS 0051796 5/1982 European Pat. Off. ......... C09J 3/14
0051797 5/1982 European Pat. Off. ......... C09J 3/14
2182186 7/1973 France ............................. A61K 5/00

OTHER PUBLICATIONS

Chemical Abstracts, vol. 111 Columbus Ohio, US; abstract No. 97785, Yoshikuni, Masako et al. Polymerization of vinyl compounds initiated by dibutylborinic acid esters & Kobunshi Ronbunshu, 46(4), 223-31, 1989.

*Primary Examiner*—Paul R. Michl
*Assistant Examiner*—LaVonda R. DeWitt
*Attorney, Agent, or Firm*—Sherman and Shalloway

[57] ABSTRACT

A dental or surgical adhesive filler containing (a) a polymerizable acrylic acid or methacrylic acid derivative, (b) a vinyl polymer powder, (c) an organic boron compound as a curing agent, and optionally, a polar organic compound and an inert diluent. The advantage of the above dental or surgical adhesive filler is that it is easy to handle due to stability in curing time and freedom of ignition.

10 Claims, No Drawings

DENTAL OR SURGICAL ADHESIVE FILLER

The present invention relates to a dental or surgical adhesive filler. More specifically, it relates to a dental or surgical adhesive filler which shows a stable curing time and is free of ignition.

Japanese Patent Publication No. 51-37092 (37,092/1976) discloses a dental or surgical adhesive filler containing, as a curing agent, a product prepared by reacting trialkylboron with 0.2 to 0.9 mol, per mole of the trialkylboron, of oxygen.

As described in the above Publication, trialkylboron is very unstable in air and very dangerous in handling, since it reacts with oxygen to ignite when exposed to air. In the curing agent proposed in the above Japanese Patent Publication No. 51-37092, the ignitability is removed from trialkylboron while preventing as much as possible the properties of the trialkylboron as the curing agent from decreasing, thereby to retain the adhesion properties. Since, however, this curing agent is prepared by reacting trialkylboron with oxygen as described above, it is not easy to constantly produce a product having a definite composition. Therefore, an adhesive filler containing this product as a curing agent cannot necessarily be said to show stable performance since its curing time is unstable. It is known that the reaction between trialkylboron and oxygen includes, for example, a reaction to form dibutyl per-borinic acid from tributylboron and oxygen (Treatises on Polymers, vol. 46, No. 4, pages 223–231, 1989).

Japanese Laid-open (Kokai) Patent Application No. 58-136602 (136,602/1983) discloses an aerobically curing resin composition containing a polymeric organic boron compound (curing agent) whose polymer matrix, stable to infiltration of air, has a hydrogen boride group and/or an organic boron group as a substituent.

Further, Japanese Laid-open (Kokai) Patent Application No. 2-50922 (50,922/1990) discloses a composition which is based on a polymerizable olefinically unsaturated compound and an organic boron compound as an initiator and shows a stable shelf life in the absence of oxygen, and this composition contains an organic boron compound having at least one B-C bond, preferably at least two B-C bonds, as a polymerization initiator, a compound having a molecular weight of 63 to 10,000 and having at least one ethylenic bond, and an inhibitor or stabilizer against anionic polymerization. As the organic boron compound, the above Publication describes 9-borabicyclo[3.3.1]nonane, diisopinocampheylborane, dicyclohexylborane, hexylborane-(2,3-dimethyl-2-butylborane), 3,5-dimethylbornane and diisoamylborane.

It is an object of the present invention to provide a dental or surgical adhesive filler.

It is another object of the present invention to provide a dental or surgical adhesive filler which shows a stable curing time and is free of ignition.

Other objects and advantages of the present invention will be apparent from the following description.

According to the present invention, the above objects and advantages of the present invention are achieved by a dental or surgical adhesive filler which contains (a) a polymerizable acrylic acid or methacrylic acid derivative, (b) a vinyl polymer powder and, as a curing agent, (e) an organic boron compound of the formula (1), $$(R^1)_n B(OR^2)_{3-n} \qquad (1)$$

wherein $R^1$ is an alkyl group, an aralkyl group or an aryl group, $R^2$ is a hydrogen atom, an alkyl group, an aralkyl group or an aryl group, the aryl portion of each of the aralkyl groups, and each of the aryl groups, being optionally substituted, and n is a number of from 0.5 to 2.8.

The adhesive filler of the present invention comprises a polymerizable acrylic acid or methaerylic acid derivative (a), a vinyl polymer powder (b) and an organic boron compound (e) as a curing agent.

As the polymerizable acrylic acid or methaerylic acid derivative (a), preferred is an ester of acrylic acid or methacrylic acid such as an ester obtained from acrylic acid or methacrylic acid and a mono-, di-, tri- or tetraol having 1 to 20 carbon atoms.

Examples of the above compound (a) preferably include methyl, ethyl, propyl, butyl, decyl or lauryl ester of (meth)acrylic acid; ethylene glycol di(meth)acrylate, diethylene glycol di(meth)acrylate, trimethylolpropane tri(meth)acrylate, pentaerythritol tetra(meth)acrylate, 2-hydroxyethyl (meth)acrylate, 2,2-bis(4-methacryloxypolyethoxyphenyl)propane and 4-methaeryloxyethyltrimellitic acid (anhydride).

The above compounds (a) may be used alone or in combination.

As the vinyl polymer powder (b), preferred is a powder of a homopolymer or copolymer of acrylic acid or methacrylic acid or derivative thereof.

Examples of the above compound preferably include acrylic acid, methacrylic acid and an ester obtained from any one of these acids and an alcohol having 1 to 30 carbon atoms.

The copolymer may also be a product obtained from acrylic acid or methacrylic acid or derivative thereof and other comonomer such as a α-olefin having 2 to 20 carbon atoms or styrene.

The vinyl polymer powder (b) may optionally contain a powder of a polymer such as polyethylene terephthalate, polybutylene terephthalate, polycarbonate or polyvinyl chloride, an inorganic powder such as a glass powder, silica or a pigment, or a powder of an organic or inorganic composite filler.

The curing agent (e) used in the filler of the present invention is an organic boron compound having the above formula (1).

In the formula (1), $R^1$ is an alkyl group, an aralkyl group or an aryl group, and $R^2$ is a hydrogen atom, an alkyl group, an aralkyl group or an aryl group. The aryl portion of each of the aralkyl groups may be optionally substituted, and each of the aryl groups may be optionally substituted. n is a number of from 0.5 to 2.8.

Each of the alkyl groups as $R^1$ and $R^2$ may be, independently, preferably a linear or branched alkyl group having 1 to 20 carbon atoms such as methyl, ethyl, n-propyl, isopropyl, isobutyl, n-pentyl, hexyl, nonyl, decyl, lauryl and stearyl.

Each of the aralkyl groups as $R^1$ and $R^2$ preferably includes independently benzyl, a α-phenetyl and β-phenetyl.

Each of the aryl groups as $R^1$ and $R^2$ preferably includes independently phenyl, naphthyl and biphenyl.

The substituent on each of the aryl portion of the aralkyl group and the aryl group preferably includes halogen atoms such as fluorine, chlorine and bromine.

n is a number of from 0.5 to 2.8, preferably from 1.0 to 2.5, more preferably from 1.5 to 2.2.

Examples of the organic boron compound (c) preferably include $(C_4H_9)_2BOC_4H_9$ and $(C_5H_{11})_{1.5}B(OC_5H_{11})_{1.5}$.

In the adhesive filler of the present invention, the amount of each of the components (a), (b) and (c) based on the total weight of the components (a), (b) and (c) are as follows.. The amount of the component (a) is preferably 24 to 75 % by weight, more preferably 36 to 62 % by weight. The amount of the component (b) is preferably 24 to 75% by weight, more preferably 36 to 62% by weight. The amount of the component (c) is preferably 1 to 16% by weight, more preferably 2 to 8% by weight.

The adhesive filler of the present invention may contain other components in addition to the above components (a), (b) and (c).

The above "other components" include a polar organic compound and an inert diluent.

Examples of the polar organic compound preferably include an alcohol, ester, ketone, amine and thiol. When added, the polar organic compound generally shows an effect that the curing rate is decreased to increase the adhesion strength. The amount of the polar organic compound based on the curing agent (c) is preferably 100 mol equivalent % or less, more preferably 10 mol equivalent % or less.

Examples of the inert diluent preferably include general aliphatic and aromatic hydrocarbons such as hexane, heptane, toluene and xylene. The amount of the inert diluent based on the curing agent (c) is preferably 200% by volume or less, more preferably 100% by volume or less.

The present invention will be detailed hereinafter by reference to Examples, which are, however, not intended to limit the present invention.

In Examples, "part" stands for "part by weight". Tests described in Examples were carried out as follows.

Ignition test: According to the spontaneous ignition test of the Fire Services Act, a curing agent (c) in an amount of 0.3 cm$^3$ or 0.5 cm$^3$ was dropped on a paper filter, and the filter was observed to see it discolored and/or ignited.

Curing test (A method): Carried out according to JIS T6509 at a temperature of 27° C. 48 Parts of a component (a), 48 parts of a component (b) and 4 parts of a component (e) were mixed to prepare an adhesive filler paste, and a curing time was determined by measuring temperatures of heat generated by the curing, using a thermocouple.

Curing test (B method): A curing time was determined in the same manner as in the method A except that a component (b) was added 1 minute, 3 minutes and 5 minutes after components (a) and (c) were mixed.

Adhesion strength: A methylmetacrylate resin rod having a diameter of 5 mm and a length of about 30 mm was vertically attached to an adherend prepared from a fresh bovine tooth (front tooth) or a Co-Cr alloy for dental molding (JIS T6115) through an adhesive filler paste to prepare a test piece. The test piece was immersed in water for 24 hours, and then subjected to a tensile tester to determine a breaking point, which was taken as an adhesion strength.

Referential Example I (Preparation of dibutylmonobutoxy boron)

182 Parts by weight of tri-n-butyl boron and 74 parts by weight of n-butanol were refluxed in a nitrogen gas atmosphere with stirring for 1 week to give an intended product.

The above product had a boron content of 5.2% by weight according to an alkali titration method (calculated: 5.46% by weight) and a purity of 95.2% according to a gas chromatography (relative area method).

Referential Exam 2 (Preparation of diamylmonoamyloxy boron)

An intended product having a boron content of 4.3% by weight (calculated: 4.50%) and a purity of 95.5% was obtained from 226 parts by weight of triisoamyl boron and 88 parts by weight of isoamyl alcohol in the same manner as in Referential Example 1.

Referential Example 3

Air equivalent to 0.5 mol of oxygen was blown into 182 parts by weight of tri-n-butyl boron over about half a day to give a 0.5 mol oxygen reaction product of tri-n-butyl boron.

Example 1

48 Parts by weight of methyl methacrylate, 4 parts by weight of the dibutylmonobutoxy boron obtained in Referential Example 1 and 48 parts by weight of a methyl methacrylate polymer powder were mixed to prepare a paste. Table 1 shows the results of the ignition test of the dibutylmonobutoxy boron and the results of the curing test and adhesion strength of the resultant paste.

Example 2

4 Parts by weight of the diamylmonoamyloxy boron obtained in Referential Example 2, 41 parts by weight of methyl methacrylate, 5 parts by weight of triethylene glycol dimethacrylate, 48 parts by weight of a methyl methacrylate powder (containing 5% by weight of a glass powder) and 0.1 part by weight of isoamyl alcohol (6.8 mol equivalent % based on the curing agent) were fully mixed to prepare a paste. Table 1 shows the results of the ignition test of the curing agent and the test results of the resultant paste.

Example 3

4 Parts by weight of the dibutylmonobutoxy boron obtained in Referential Example 1, 24 parts by weight of butyl acrylate, 24 parts by weight of methyl methacrylate, 48 parts by weight of a methyl methacrylate/α-methylstyrene copolymer powder (copolymerization ratio = 1/1 (molar ratio)) and 7 parts by weight of hexane (194% by volume based on the curing agent) were fully mixed to prepare a paste. Table 1 shows the results of the ignition test of the curing agent and the test results of the resultant paste.

Comparative Example 1

A paste was prepared in the same manner as in Example 1 except that the dibutylmonobutoxy boron was replaced with the oxygen reaction product of tri-n-butyl boron obtained in Referential Example 3. Table 1 shows the results of the ignition test of the curing agent and the test results of the paste. The oxygen reaction product of tri-n-butyl boron had high ignition capability, and as is clear from the test result of its curing test (B method), the past thereof lacked stability in the curing time.

TABLE 1

| | Ignition test | | Curing time (minutes, second) | | | | Adhesion strength (kg/cm²) | | |
|---|---|---|---|---|---|---|---|---|---|
| | 0.3 cm³ | 0.5 cm³ | A method | B method After 1 min. | After 3 min. | After 5 min. | Enamel | Dentine | Alloy |
| Example 1 (Ref. Example 1) | Scorched brown | Scorched black | 8'40" | 9'00" | 9'30" | 10'00" | 131 | 156 | 187 |
| Example 2 (Ref. Example 2) | Scorched brown | Scorched black | 10'10" | 10'30" | 11'00" | 11'30" | 160 | 173 | 191 |
| Example 3 (Ref. Example 1) | Scorched brown | Scorched black | 9'00" | 9'15" | 9'45" | 10'15" | 143 | 159 | 188 |
| Comp. Example 1 (Ref. Example 3) | Scorched black | Ignited | 8'10" | 8'30" | 11'00" | 12'00" | 132 | 158 | 184 |

What is claimed is:

1. A dental or surgical adhesive filler which contains (a) a polymerizable acrylic acid or methacrylic acid derivative, (b) a vinyl polymer powder and, as a curing agent, (c) an organic boron compound of the formula (1),

$$(R^1)_n B(OR^2)_{3-n} \qquad (1)$$

wherein $R^1$ is an alkyl group, an aralkyl group or an aryl group, $R^2$ is a hydrogen atom, an alkyl, group, an aralkyl group or an aryl group, the aryl portion of each of said aralkyl groups, and each of said aryl groups, being optionally substituted, and n is a number of from 0.5 to 2.8.

2. The adhesive filler of claim 1, wherein the polymerizable acrylic acid or methacrylic acid derivative (a) is an ester of acrylic acid or methacrylic acid derivative.

3. The adhesive filler of claim 1, wherein the vinyl polymer powder (b) is a powder of a homopolymer or copolymer of acrylic acid or methaerylic acid or derivative thereof.

4. The adhesive filler of claim 1, wherein each of the alkyl groups as $R^1$ and $R^2$ in the formula (1) is independently a linear or branched alkyl group having 1 to 20 carbon atoms.

5. The adhesive filler of claim 1, wherein each of the aralkyl groups as $R^1$ and $R^2$ in the formula (1) is independently benzyl, α-phenetyl or β-phenetyl.

6. The adhesive filler of claim 1, wherein each of the aryl groups as $R^1$ and $R^2$ in the formula (1) is independently phenyl, naphthyl or biphenyl.

7. The adhesive filler of claim 1, wherein the n in the formula (1) is 1.0 to 2.5.

8. The adhesive filler of claim 1, wherein, based on the total amount of the polymerizable acrylic acid or methaerylic acid derivative (a), the vinyl polymer powder (b) and the organic boron compound (c), the amount of the polymerizable acrylic acid or methacrylic acid derivative (a) is 24 to 75% by weight, the amount of the vinyl polymer powder (b) is 24 to 75% by weight and the amount of the organic boron compound (c) is 1 to 16% by weight.

9. The adhesive filler of claim 1, wherein there is further contained a polar organic compound in an amount of 100 mol equivalent % or less based on the organic boron compound (c).

10. The adhesive filler of claim 1, wherein there is further contained an inert diluent in an amount of 200% by volume or less based on the organic boron compound (c).

* * * * *